United States Patent [19]

Plath et al.

[11] Patent Number: 4,808,212
[45] Date of Patent: Feb. 28, 1989

[54] OXIME ESTERS OF SUBSTITUTED QUINOLINE-8-CARBOXYLIC ACIDS AND USE THEREOF AS HERBICIDES

[75] Inventors: Peter Plath, Frankenthal; Karl Eicken, Wachenheim; Bernd Zeeh, Limburgerhof; Ulrich Eichenauer, Frankfurt; Helmut Hagen, Frankenthal; Rolf-Dieter Kohler, Edingen-Neckarhausen; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 944,519

[22] Filed: Dec. 22, 1986

[30] Foreign Application Priority Data

Dec. 23, 1985 [DE] Fed. Rep. of Germany ....... 3545904

[51] Int. Cl.$^4$ ................. C07D 215/48; C07D 405/12; C07D 409/12; A01N 43/42
[52] U.S. Cl. ....................... 71/94; 546/170; 71/90; 71/92
[58] Field of Search .................. 546/170; 71/94, 90

[56] References Cited

U.S. PATENT DOCUMENTS 3,592,920  7/1971  Gutman et al. ............. 424/327
4,497,651  2/1985  Hagen et al. .............. 71/94
4,632,696  12/1986 Hagen et al. .............. 71/94

FOREIGN PATENT DOCUMENTS 47-37540  9/1972  Japan.

Primary Examiner—Glennon H. Hollrah
Assistant Examiner—D. B. Springer
Attorney, Agent, or Firm—Keil & Weinkauf

[57] ABSTRACT

Oxime esters of substituted quinoline-8-carboxylic acids of the formula

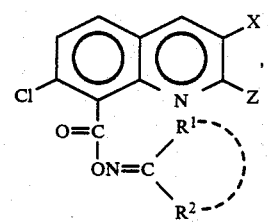

where X is hydrogen, $C_1$–$C_4$-alkyl or halogen, Z is hydrogen or methyl, $R^1$ is $C_1$–$C_6$-alkyl, $C_1$–$C_4$-alkoxymethyl, $C_1$–$C_4$-alkoxyethyl, $C_1$–$C_4$-alkylthiomethyl, $C_1$–$C_4$-alkylthioethyl, $C_1$–$C_4$-alkoxycarbonyl, $C_3$–$C_6$-alkenyl or $C_5$–$C_8$-cycloalkyl, each of which is unsubstituted or bears up to 3 methyl substituents, hydrogen, cyano, acetyl, benzoyl, unsubstituted benzyl or phenyl, or benzyl or phenyl bearing up to 3 substitutents selected from the group consisting of halogen, cyano, trifluoromethyl, $C_1$–$C_4$-haloalkyloxy, $C_1$–$C_6$-alkylthio, $C_1$–$C_4$-alkoxy, $C_1$–$C_4$-alkyl, hydroxy, dimethylamino or acetamino, $R^2$ is hydrogen if $R^1$ is not hydrogen, $R^2$ further denotes $C_1$–$C_6$-alkyl, $C_1$–$C_4$-alkoxymethyl, chloromethyl, azolylmethyl, 1,1-dimethoxymethyl, cyano, $C_1$–$C_4$-alkoxycarbony, $C_1$–$C_4$-alkoxy, phenyl if $R^1$ is H, $CH_3$ or acetyl, or $R^2$ denotes, when $R^1$ is H or methyl, furyl, tetrahydrofuryl, thienyl, tetrahydropyranyl, tetrahydrothiopyranyl, dihydro-$\Delta^3$-pyranyl or dihydro-$\Delta^3$-thiopyranyl; further, $R^1$ and $R^2$, together with the carbon atom to which they are linked, denote $C_1$–$C_{12}$-cycloalkylidene, $C_5$–$C_6$-cycloalkenylidene or 4-oxacyclohexadienylidene, each of which is unsubstituted or bears up to 3 methyl substituents, it being possible, where the ring is 5-membered or 6-membered, or doubly unsaturated 6-membered, for it to contain an oxygen or sulfur atom, their preparation, and their use as herbicides.

6 Claims, No Drawings

OXIME ESTERS OF SUBSTITUTED QUINOLINE-8-CARBOXYLIC ACIDS AND USE THEREOF AS HERBICIDES

It is known from European Patent Application Nos. 60,429 and 104,389 that esters of herbicidal quinoline-8-carboxylic acid have herbicidal properties. However, the specific action of these esters is in every case hugely inferior to that of the free acid.

We have now found that oxime esters which are derived from quinoline-8-carboxylic acids and have the general formula I

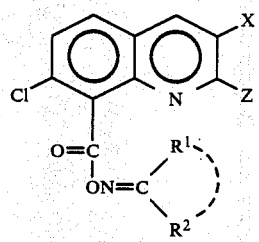

Where X is hydrogen, $C_1$–$C_4$-alkyl or halogen, Z is hydrogen or methyl, $R^1$ is $C_1$–$C_6$-alkyl, $C_1$–$C_4$-alkoxymethyl, $C_1$–$C_4$-alkoxyethyl, $C_1$–$C_4$-alkylthiomethyl, $C_1$–$C_4$-alkylthioethyl, $C_1$–$C_4$-alkoxycarbonyl, $C_3$14 $C_6$-alkenyl or $C_5$–$C_8$-cycloalkyl, each of which is unsubstituted or bears up to 3 methyl substituents, hydrogen, cyano, acetyl, benzoyl, unsubstituted benzyl or phenyl, or benzyl or phenyl bearing up to 3 substituents selected from the group consisting of halogen, cyano, trifluoromethyl, $C_1$–$C_4$-haloalkyloxy, $C_1$–$C_6$-alkylthio, $C_1$–$C_4$-alkoxy, $C_1$–$C_4$-alkyl, hydroxy, dimethylamino or acetamino, $R^2$ is hydrogen if $R^1$ is not hydrogen, $R^2$ further denotes $C_1$–$C_6$-alkyl, $C_1$–$C_4$-alkoxymethyl, chloromethyl, azolylmethyl, 1,1-dimethoxymethyl, cyano, $C_1$–$C_4$-alkoxycarbonyl, $C_1$–$C_4$-alkoxy, phenyl if $R^1$ is H, $CH_3$ or acetyl, or $R^2$ denotes, when $R^1$ is H or methyl, furyl, tetrahydrofuryl, thienyl, tetrahydropyranyl, tetrahydrothiopyranyl, dihydro-$\Delta^3$-pyranyl or dihydro-$\Delta^3$-thiopyranyl; further, $R^1$ and $R^2$, together with the carbon atom to which they are linked, denote $C_1$–$C_{12}$-cycloalkylidene, $C_5$–$C_6$-cycloalkenylidene or 4-oxacyclohexadienylidene, each of which is unsubstituted or bears up to 3 methyl substituents, it being possible, where the ring is 5-membered or 6-membered, or doubly unsaturated 6-membered, for it to contain an oxygen or suflur atom, have a more powerful herbicidal action than the quinoline esters hitherto disclosed. We have also found that the compounds of the formula I are more suitable than the parent quinoline carboxylic acids for the desired weed control at the postemergence stage, ie. through absorption of the active substances of the formula I via the plant leaves. In the light of the reduced action of all hitherto disclosed esters of quinolinecarboxylic acids, this property was not foreseeable and has to be regarded as surprising.

$C_1$–$C_6$-alkyl includes not only straight-chain but also branched paraffin hydrocarbons of 1 to 6 carbon atoms, such as methyl, ethyl, propyl, isopropyl, butyl, isobutyl, tert.-butyl, sec.-amyl, isoamyl, n-pentyl or n-hexyl.

$C_1$–$C_4$-alkoxymethyl is for example methoxymethyl, ethoxymethyl, isopropoxymethyl or n-butoxymethyl, while $C_1$–$C_4$-alkoxyethyl is for example 1-methoxyethyl, 2-methoxyethyl, 2ethoxyethyl and the like.

$C_1$–$C_4$-alkylthioethyl comprises 2-methylthioethyl, 1-methylthioethyl, 2-isopropylthioethyl, 2-isobutylthioethyl and the like.

Halogen can be fluorine, chlorine, bromine or iodine. Substituted phenyl is for example 4-fluorophenyl, 2-chlorophenyl, 3-chlorophenyl, 4-chlorophenyl, 4-bromophenyl, 4-cyanophenyl, 4-trifluoromethylphenyl, 4-methoxyphenyl, 3-methoxyphenyl, 2-methylphenyl, 3-methylphenyl, 4-methylphenyl, 2-hydroxyphenyl, 4-dimethylaminophenyl, 4-acetaminophenyl, 3,4-dichlorophenyl, 2,4-dichlorophenyl, 2,6-dichlorophenyl, 3,5-dibromo-4-hydroxyphenyl or 3,5-diiodo-4-hydroxyphenyl.

$C_3$–$C_6$-alkenyl includes unsaturated straightchain or branched hydrocarbon radicals of up to 6 carbon atoms in the chain, eg. allyl, butenyl, isobutenyl, pentenyl, isopentenyl or hexenyl.

$C_5$–$C_8$-cycloalkyl includes for example cyclopentyl, cyclohexyl, 3,3,5-trimethylcyclohexyl, cycloheptyl or cyclooctyl.

Azolylmethyl is pyrazolylmethyl, imidazolylmethyl or triazolylmethyl.

When $R^1$ and $R^2$ are combined with the carbon atoms to which they are bonded to form a saturated or unsaturated ring which may be substituted by methyl and may contain an oxygen or sulfur in the ring, the oximes of the following ketones are covered: cyclobutanone, cyclopentanone, 3-methylcyclopentanone, 3-methylcyclopent-2-en-1-one, cyclohexanone, 2-methylcyclohexanone, 3-methylcyclohexanone, 4-methylcyclohexanone, 3,3,5-trimethylcyclohexanone, isophorone, cyclohex-2-en-1-one, cycloheptanone, cyclooctanone, cyclododecanone, tetrahydrothiopyran-4-one, 2,6-dimethyltetrahydrothiopyran-4-one, 2,6-dimethyltetrahydropyran-4-one, 2,6-dimethylpyran-4-one, tetrahydropyran-4-one, thiopyran-4-one, 2,6-dimethylthiopyran-4-one, tetrahydrofuran-3-one, benzoquinone, toluquinone, xyloquinone and the like.

The novel compounds of the formula I are obtained by reacting for example an acid chloride of the formula II (prepared from the known quinoline-8-carboxylic acids as described in EP No. 60,429) with an oxime $R^1R^2C$=N—OH at from −10° C. to 120° C., preferably from 10° C. to 50° C., in an inert solvent in the presence of a baase. Suitable solvents are pyridine, toluene, chlorobenzene, methylene chloride, methyl tert.-butyl ether, tetrahydrofuran and the like. As suitable bases pyridine, triethylamine, 1,8-diazabicyclo[5.4.0]undec-7-one (=DBU) or, in the prepatation by Schotten-Baumann, aqueous alkali metal hydroxide solution or alkali metal carbonate solution.

The $R^1R^2C$=NOH oximes used are known compounds or can be obtained in the customary manner which follows from the respective structural formula. Oximes of saturated (aliphatic) or olefinically unsaturated ketones or of olefinically unsaturated or aromatic aldehydes are preferred on account of the particularly smooth course of reaction.

The reaction product is worked up, if pyridine is used, by pouring into water, but if a water-immiscible solvent is used by extraction with water, washing with dilute mineral acid, deacidifying, drying and evaporating under reduced pressure. The synthesis of esters of benzaldoximes is generally only possible with the pyridine variant, since the products decompose when hot or in the presence of strong acids to benzonitriles and the known quinolinecarboxylic acids.

The oximes of the formula III are usually present in the form of a mixtures of their syn- and anti-isomers. For that reason the compounds of the formula I can likewise be obtained in the form of syn-/anti-isomer mixtures. No isomers appear if oximes of symmetrical ketones such as acetone, cyclopentanone, cyclohexanone etc. are used.

If the crude products need to be purified, this is easily done in the case of esters of ketoximes by recrystallizing from ethyl acetate or the like, while the oxime esters of benzaldehydes are epedientlly purified by reprecipitating from ethanol/water or by chromatography.

EXAMPLE 1

Acetone oxime esters of 3,7-dichloroquinoline-8-carboxylic acid 95 g (1.2 mol) of pyridine are added to a solution of 87.6 g (1.2 mol) of acetone oxime in 1.5 l of methylene chloride, followed by adding 260.5 g (1 mol) of 3,7-dichloroquinoline-8-carbonyl chloride a little at a time with ice cooling to maintain the temperature within the range from 15° to 20° C. After 8 hours of stirring at 25° C. the reaction mixture is extracted twice with 200 ml of 5% strength HCl and washed once with water. The organic phase is then separated off and dried over MgSO4, and the methylene chloride is driven off under reduced pressure. The residue is recrystallized from ethyl acetate and dried under reduced pressure to leave 240 g (81%) of a white powder having a melting point of 131°–132° C.

EXAMPLE 2

Benzaldehyde oxime ester of 3,7-dichloroquinoline-8-carboxylic acid (compound No. 16 of Table I)

6.7 g (55 mmol) of benzaldehyde oxime are dissolved in 50 ml of pyridine, and 13 g (50 mol) of 3,7-dichloroquinoline-8-carbonyl chloride are added at 0° C. a little at a time. After 3 hours of stirring the reaction mixture is poured into a mixture of 100 ml of ice-water and 50 ml of glacial acetic acid, and the precipitated solid is filtered off with suction, stirred up with 150 ml of NaHCO3 solution, is filtered off again with suction and washed with water. Drying under reduced pressure leaves 9 g of a pale brown solid (53% yield) having a melting point of 166°–168° C.

EXAMPLE 3

Cyclohexane oxime ester of 3,7-dichloroquinoline-8-carboxylic acid (compount No. 57 in Table II)

13 g (50 mol) of 3,7-dichloroquinoline-8-carbonyl chloride are added at 15°–20° C. a little at a time to an ice-cooled solution of 11.3 g (0.1 mol) of cyclohexanone oxime in 100 ml of pyridine. After 3 hours of stirring the pyridine is removed in a rotary evaporator, and the residue is dissolved in CH2Cl2, washed with water, dried (MgSO4) and evaporated to dryness. The precipitated solid is recrystallized from diisopropyl ether and pentane (7:3).

Yield: 9.5 g (57%) of a white powder, melting point 142°–143° C.

By appropriately modifying the above examples it is possible to prepare the remaining compounds which are listed in Tables I and II and for the characterization of which the tables provide physical data. The compounds for which no physical data are shown can be obtained in a corresponding manner; owing to their structure as oxime esters of herbicidal quinolinecarboxylic acids, they can likewise be expected to have a powerful herbicidal action.

TABLE I

| No. | X | R$^1$ | R$^2$ | m.p. (°C.) |
|---|---|---|---|---|
| 1 | CH$_3$ | CH$_3$ | CH$_3$ | 111–112 |
| 2 | Cl | CH$_3$ | CH$_3$ | 131–132 |
| 3 | Cl | C$_2$H$_5$ | CH$_3$ | 130–132 |
| 5 | Cl | n-C$_3$H$_7$ | n-C$_3$H$_7$ | 76–78 |
| 7 | Cl | i-C$_4$H$_9$ | i-C$_4$H$_9$ | 92–94 |
| 8 | Cl | CH$_3$ | neopentyl | 133–134 |
| 9 | Cl | CH$_3$ | 4-methylpentyl | 92–94 |
| 10 | Cl | —(CH$_2$)$_2$—CH=C(CH$_3$)$_2$ | CH$_3$ | 74–75 |
| 11 | Cl | CH$_3$ | CH$_2$—OCH$_3$ | 105–107 |
| 12 | Cl | C$_2$H$_5$ | CH$_2$OCH$_3$ | 86–88 |
| 13 | Cl | CH$_3$ | CH(OCH$_3$)$_2$ | 117–118 |
| 14 | Cl | —CH(CH$_3$)—S—CH$_3$ | CH$_3$ | 118–119 |
| 15 | Cl | benzyl | CH$_3$ | |
| 16 | Cl | H | phenyl | 166–168 |
| 17 | Cl | CH$_3$ | phenyl | 173–174 |
| 18 | Cl | phenyl | —CH$_2$Cl | |
| 19 | Cl | phenyl | 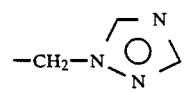 | 185–186 |

TABLE I-continued

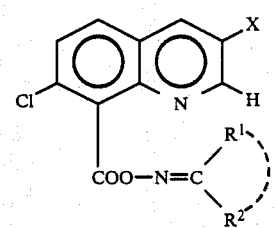

| No. | X | R¹ | R² | m.p. (°C.) |
|---|---|---|---|---|
| 20 | Cl | acetyl | CH₃ | 114–115 |
| 21 | Cl | acetyl | phenyl | 167–169 |
| 22 | Cl | 4-N(CH₃)₂—phenyl | H | 165–166 |
| 23 | Cl | 2-Cl—phenyl | H | 158–160 |
| 24 | Cl | 3-Cl—phenyl | H | 155–158 |
| 25 | Cl | 4-Cl—phenyl | H | 175–177 |
| 26 | Cl | 4-F—phenyl | H | 155–157 |
| 27 | Cl | 4-CF₃—phenyl | H | 182–183 |
| 28 | Cl | 4-CH₃—phenyl | H | 165–167 |
| 29 | Cl | 4-CH₃O—phenyl | H | 147–149 |
| 30 | Cl | 3-CH₃—phenyl | H | 121–123 |
| 31 | Cl | 3-CH₃O—phenyl | H | 141–143 |
| 32 | Cl | 3-F₃CH—CF₂O)—phenyl | H | 138–140 |
| 33 | Cl | 4-H₃CCONH—phenyl | H | 174–176 |
| 34 | Cl | 4-CN—phenyl | H | 178–180 |
| 35 | Cl | 3,4-Cl₂—phenyl | H | — |
| 36 | Cl | 2,4-Cl₂—phenyl | H | 162–163 |
| 37 | Cl | 2,4-(n-C₆H₁₃—S)₂—phenyl | H | — |
| 38 | CH₃ | CH₃ | C₂H₅ | 74–76 |
| 39 | CH₃ | CH₃ | i-C₃H₇ | 97–98 |
| 40 | CH₃ | n-C₃H₇ | n-C₃H₇ | 92–93 |
| 41 | CH₃ | i-C₄H₉ | i-C₄H₉ | 70–72 |
| 42 | Cl | 2-thienyl | CH₃ | 127–129 |
| 43 | CH₃ | 3-thienyl | CH₃ | 137–138 |
| 44 | Cl | 2-furyl | H | — |
| 45 | Cl | 2-furyl | CH₃ | 163–164 |
| 46 | Cl | 5,6-dihydro-3-thiopyranyl-3 | H | 225–228 |
| 47 | Cl | 5,6-dihydro-3-pyranyl-3 | CH₃ | 159–161 |
| 48 | Cl | 2-furyl | n-C₃H₇ | — |
| 49 | Cl | 2,3-dihydro-6-methyl-5-pyran-6-yl | | |
| 50 | Cl | 4-hydroxy-3,5-dibromophenyl | H | 203–205 |
| 51 | Cl | 4-hydroxy-3-5,diiodophenyl | H | |
| 52 | Cl | CH₃ | OC₂H₅ | 129–130 |
| 53 | Cl | CN | CO₂C₂H₅ | 138–139 |
| 54 | Cl | 3-thienyl | CH₃ | 160–162 |
| 55 | CH₃ | 4-CF₃—phenyl | H | 135–137 |
| 56 | CH₃ | 2-Cl—phenyl | CH₃ | 160–162 |

TABLE II

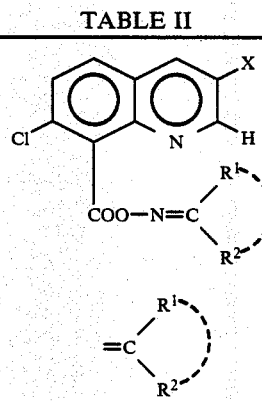

| No. | X | | m.p. (°C.) |
|---|---|---|---|
| 57 | Cl | cyclopentylidene | 128–130 |
| 58 | CH₃ | cyclopenytlidene | 105–107 |
| 59 | Cl | cyclohexylidene | 142–143 |
| 60 | CH₃ | cyclohexylidene | — |
| 61 | Cl | 3,3,5-trimethylcyclohexylidene | 144–145 |

TABLE II-continued

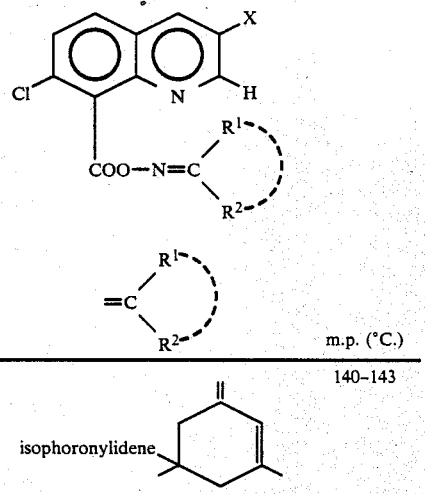

| No. | X | | m.p. (°C.) |
|---|---|---|---|
| 62 | Cl | isophoronylidene | 140–143 |
| 63 | Cl | 3-methylcyclopentylidene | 132–133 |
| 64 | Cl | 3-methylcyclohexylidene | 122–125 |
| 65 | Cl | 3-methyl-cyclopent-2-enylidene | 150 |

TABLE II-continued

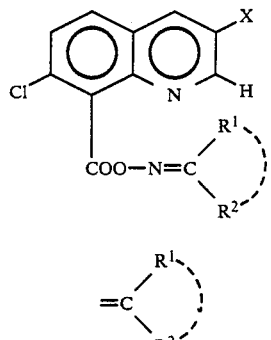

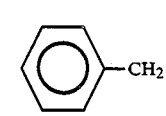

| No. | X | =C(R¹)(R²) | m.p. (°C.) |
|---|---|---|---|
| 66 | Cl | cyclohex-2-enylidene | |
| 67 | Cl | cycloheptylidene | 120–122 |
| 68 | Cl | 2,6-dimethylpyranylidene-4 | — |
| 69 | Cl | 2,6-dimethylthiopyranylidene-4 | — |
| 70 | Cl | tetrahydrothiopyranylidene-4 | 167–168 |
| 71 | Cl | tetrahydropyranylidene-4 | 153–155 |
| 72 | Cl | cyclododecylidene | 164–166 |
| 73 | Cl | 2,3-benzocyclopentylidene-1 | 164–165 |
| 74 | $CH_3$ | 2,3-benzocyclopentylidene-1 | 175–176 |
| 75 | Cl | 2,3-benzocyclohexylidene-1 | 178–179 |
| 76 | $CH_3$ | 2,3-benzocyclohexylidene-1 | 180–181 |
| 77 | $CH_3$ | 3,3,5-trimethylcyclohexylidene | 123–125 |
| 78 | $CH_3$ | isophoronylidene | 118–120 |
| 79 | $CH_3$ | 3-methylcyclopent-2-enylidene | |
| 80 | $CH_3$ | cycloheptylidene | 108–110 |
| 81 | $CH_3$ | 2,6-dimethylpyranylidene-4 | — |
| 82 | $CH_3$ | tetrahydropyranylidene-4 | 134–135 |
| 83 | $CH_3$ | tetrahydrothiopyranylidene-4 | 172–173 |

The following compounds of the formula I may be prepared in the same manner:

| No. | X | Z | R¹ | R² |
|---|---|---|---|---|
| 84 | $C_2H_5$ | H | $CH_3$ | $CH_3$ |
| 85 | $i\text{-}C_3H_7$ | H | $CH_3$ | $CH_3$ |
| 86 | Br | H | $CH_3$ | $CH_3$ |
| 87 | $C_4H_9$ | H | $CH_3$ | $CH_3$ |
| 88 | Cl | $CH_3$ | $CH_3$ | $CH_3$ |
| 89 | H | $CH_3$ | $CH_3$ | $C_2H_5$ |
| 90 | $CH_3$ | H | $CH_2-CH_2-S-CH_3$ | $CH_3$ |
| 91 | $CH_3$ | H | $-CH(CH_3)SCH_3$ | $CH_3$ |
| 92 | $CH_3$ | H | phenyl-$CH_2$ | $CH_3$ |
| 93 | $CH_3$ | H | 2-thienyl | $CH_3$ |
| 94 | Cl | H | phenyl | pyrazolylmethyl |
| 95 | Cl | H | phenyl | imidazolylmethyl |
| 96 | $CH_3$ | H | phenyl | $-CH_2-Cl$ |
| 97 | $CH_3$ | H | $CH_3$ | $-CH(OCH_3)_2$ |
| 98 | Cl | H | $C_2H_5$ | $C_2H_5$ |
| 99 | Cl | H | $n\text{-}C_4H_9$ | $n\text{-}C_4H_9$ |
| 100 | Cl | H | $iso\text{-}C_5H_{11}$ | $CH_3$ |
| 101 | Cl | H | allyl | $CH_3$ |
| 102 | Cl | H | $CH_2-CH=CH-CH_3$ | $CH_3$ |
| 103 | Cl | H | cyclopentyl | $CH_3$ |
| 104 | Cl | H | cyclohexyl | $CH_3$ |
| 105 | Cl | H | cyclooctyl | $CH_3$ |
| 106 | Cl | H | 2,6-$Cl_2$—phenyl | H |
| 107 | Cl | H | 2,4,6-$(CH_3)_3$—phenyl | H |
| 108 | $CH_3$ | H | phenyl | H |
| 109 | $CH_3$ | H | 4-Cl—phenyl | H |

Use examples

The action on broadleaved weeds was investigated, the following plants being employed: *Avena sativa, Galium aparine, Lamium amplexicaule, Triticum aestivum* and *Veronica* spp.

On postemergence application of 3.0 kg/ha of the compound of Example 1, *Galium aparine* is well controlled. Oats, as an example of a crop plant, suffered no damage whatsoever (Table I).

On application of 0.5 kg/ha of an agent based on the compound of Example 2, wheat remained completely undamaged. The active ingredient exhibited selective herbicidal properties (Table II).

In view of the spectrum of weeds which can be combated, the tolerance of the novel compounds by crop plants or the desired influence on their growth, and in view of the numerous application methods, the novel compounds may be used in a large number of crops, for example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Picea abies* | Norway spruce |
| *Abies alba* | fir trees |
| *Pinus* spp. | pine trees |

| Botanical name | Common name |
| --- | --- |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |

| Botanical name | Common name |
| --- | --- |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel quinolinecarboxylic acid derivatives may be mixed and applied together with numerous representatives of other herbicidal or growth-regulating active ingredient groups.

It may also be useful to apply the compounds of the formula I in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE III

Control of *Echinochloa crus-galli* in rice on pre- and postemergence application of novel compounds in the greenhouse

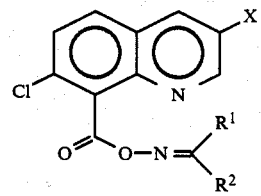

| Ex. no. | X | $R^1$ | $R^2$ | kg/ha | Type of application | Oryza sativa | Echinochloa crus-galli |
| --- | --- | --- | --- | --- | --- | --- | --- |
| 20 | Cl | acetyl | methyl | 0.25 | preemergence | 0 | 95 |
| 21 | Cl | acetyl | phenyl | 0.5 | " | 10 | 98 |
| 12 | Cl | ethyl | methoxymethyl | 0.5 | " | 0 | 95 |
| 5 | Cl | propyl | propyl | 0.5 | postemergence | 10 | 90 |
| 20 | Cl | acetyl | methyl | 0.125 | " | 0 | 90 |
| 12 | Cl | ethyl | methoxymethyl | 0.25 | " | 0 | 90 |
| 3 | Cl | ethyl | methyl | 0.5 | " | 10 | 95 |

To combat *Echinochloa crus-galli*, an important weed in rice, compounds nos. 20, 21 and 12 are suitable on preemergence application and compounds nos. 5, 20, 12 and 3 on postemergence application. Only slight damage, if any at all, is caused to the crop plant.

TABLE IV

Examples showing herbicidal action and tolerance by a crop plant on postemergence application in the greenhouse

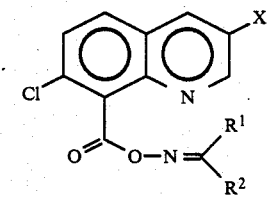

| Ex. no. | X | $R^1$ | $R^2$ | kg/ha | Triticum aestivum | Gallium aparine | Veronica spp. |
| --- | --- | --- | --- | --- | --- | --- | --- |
| 13 | Cl | methyl | $CH(OH_3)_2$ | 0.25 | 10 | 90 | 90 |
| 10 | Cl | $(CH_2CH=C(CH_3)_2)$ | methyl | 0.5 | 0 | 90 | 98 |
| 20 | Cl | acetyl | methyl | 0.5 | 0 | 95 | 98 |
| 16 | Cl | H | phenyl | 0.5 | 0 | 90 | 98 |

For controlling broadleaved unwanted plants on postemergence application, active ingredients 13, 10, 20 and 16 are suitable. Wheat, as an example of a graminaceous crop, is only slightly damaged, if at all. The compounds are selective herbicidal active ingredients.

TABLE V

Control of wanted plant growth and tolerance by a crop; preemergence application in the greenhouse

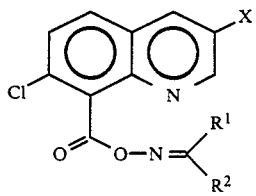

| Ex. no. | X | $R^1$ | $R^2$ | kg/ha | Triticum aestivum | Echinochloa c. g. | Gallium aparine | Veronica spp. |
|---|---|---|---|---|---|---|---|---|
| 13 | Cl | methyl | CH(OH$_3$)$_2$ | 0.5 | 10 | 98 | 90 | 100 |
| 20 | Cl | acetyl | methyol | 0.25 | 10 | 98 | 90 | 100 |

Compounds 13 and 20 are excellently tolerated by wheat, and offer good control of grassy and broadleaved unwanted plants.

We claim:

1. An oxime ester of a substituted quinoline-8-carboxylic acid of the formula

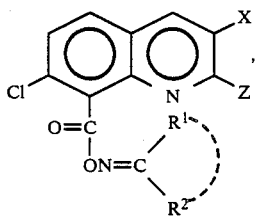

where X is hydrogen, $C_1$-$C_4$-alkyl or halogen, Z is hydrogen or methyl, $R^1$ is $C_1$-$C_6$-alkyl, $C_1$-$C_4$-alkoxymethyl, $C_1$-$C_4$-alkoxyethyl, $C_1$-$C_4$-alkylthiomethyl, $C_1$-$C_4$-alkylthioethyl, $C_1$-$C_4$-alkoxycarbonyl, $C_3$-$C_6$-alkenyl or $C_5$-$C_8$-cycloalkyl, each of which is unsubstituted or bears up to 3 methyl substituents, hydrogen, cyano, acetyl, benzoyl, unsubstituted benzyl or phenyl, or benzyl or phenyl bearing up to 3 substituents selected from the group consisting of halogen, cyano, trifluoromethyl, $C_1$-$C_4$-haloalkyloxy, $C_1$-$C_6$-alkylthio, $C_1$-$C_4$-alkoxy, $C_1$-$C_4$-alkyl, hydroxy, dimethylamino or acetamino, $R^2$ is hydrogen if $R^1$ is not hydrogen, $R^2$ further denotes $C_1$-$C_6$-alkyl, $C_1$-$C_4$-alkoxymethyl, chloromethyl, azolylmethyl, 1,1-dimethoxymethyl, cyano, $C_1$-$C_4$-alkoxycarbonyl, $C_1$-$C_4$-alkoxy, phenyl if $R^1$ is H, $CH_3$ or acetyl, or $R^2$ denotes, when $R^1$ is H or methyl, furyl, tetrahydrofuryl, thienyl, tetrahydropyranyl, tetrahydrothiopyranyl, dihydro-$\Delta^3$-pyranyl or dihydro-$\Delta^3$-thiopyranyl; further, $R^1$ and $R^2$, together with the carbon atom to which they are linked, denote $C_1$-$C_{12}$-cycloalkylidene, $C_5$-$C_6$-cycloalkenylidene or 4-oxacyclohexadienylidene, each of which is unsubstituted or bears up to 3 methyl substituents, it being possible, where the ring is 5-membered or 6-membered, or doubly unsaturated 6-membered, for it to contain an oxygen or sulfur atom.

2. A herbicidal composition containing an effective amount of a compound of the formula I in claim 1, and an inert diluent.

3. An oxime ester of the formula I as defined in claim 2, wherein X is Cl and $R^1$ and $R^2$ are each $CH_3$.

4. A method of eliminating undesirable plant growth which comprises: applying to the plants or to the soil in which the plants will grow a herbicidally effective amount of an oxime ester as defined in claim 1.

5. A method of eliminating undesirable plant growth which comprises: applying to the plants or to the soil in which the plants will grow a herbicidally effective amount of an oxime ester as defined in claim 3.

6. A herbicidal composition which comprises a carrier or diluent and a herbicidally effective amount of the oxime ester of claim 3.

* * * * *